(12) United States Patent
Taylor

(10) Patent No.: US 10,751,223 B1
(45) Date of Patent: Aug. 25, 2020

(54) PAINLESS BANDAGE REMOVAL SYSTEM

(71) Applicant: Tracy Hunter Taylor, Longview, TX (US)

(72) Inventor: Tracy Hunter Taylor, Longview, TX (US)

(*) Notice: Subject to any disclaimer, the term of this patent is extended or adjusted under 35 U.S.C. 154(b) by 104 days.

(21) Appl. No.: 15/864,059

(22) Filed: Jan. 8, 2018

(51) Int. Cl.
*A61F 13/02* (2006.01)

(52) U.S. Cl.
CPC .................. *A61F 13/0253* (2013.01)

(58) Field of Classification Search
CPC .............. A61F 13/0253; A61F 13/0246; A61F 13/025; A61F 13/02
USPC .......................................................... 602/154
See application file for complete search history.

(56) References Cited

U.S. PATENT DOCUMENTS

| | | | | |
|---|---|---|---|---|
| 5,120,349 A * | 6/1992 | Stewart | .................. | A01N 25/28 264/4.32 |
| 5,156,911 A * | 10/1992 | Stewart | ................. | A61L 15/585 428/355 AC |
| 5,387,450 A * | 2/1995 | Stewart | ................. | A61L 15/585 428/40.4 |
| 5,412,035 A * | 5/1995 | Schmitt | .................. | C09J 109/06 525/93 |
| 6,989,471 B2 * | 1/2006 | Schmidt | ................ | A61F 13/475 604/359 |
| 8,450,554 B2 * | 5/2013 | Robinson | ............ | A61F 13/0203 602/54 |
| 8,828,181 B2 * | 9/2014 | Burch | ........................ | C09J 9/00 156/334 |
| 8,946,499 B2 * | 2/2015 | Iyer | ......................... | A61L 15/42 602/41 |

FOREIGN PATENT DOCUMENTS

WO  WO-9712561 A2 * 4/1997 ......... A61F 13/0269

* cited by examiner

*Primary Examiner* — Kristen Matter
(74) *Attorney, Agent, or Firm* — Jeffrey Roddy

(57) ABSTRACT

A painless bandage removal system includes a bandage with at least one adhesive, an adhesive solvent and at least one adhesive solvent release agent. The adhesive solvent release agent includes microbeads that contain a composition that liquefies at a temperature between 42° C. and 46° C. The released solvent degrades the adhesive agent and permits painless removal of the adhered bandage.

7 Claims, 5 Drawing Sheets

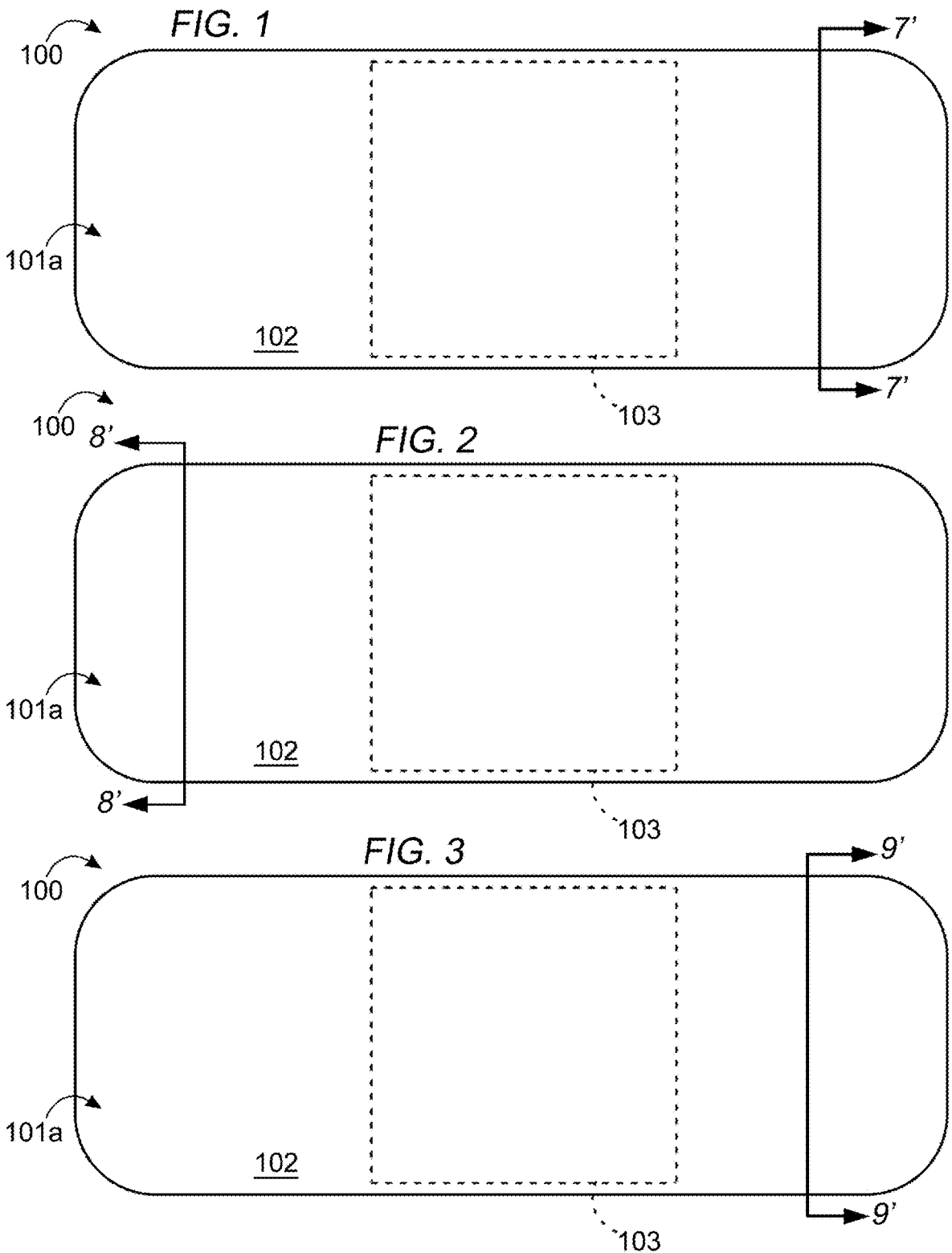

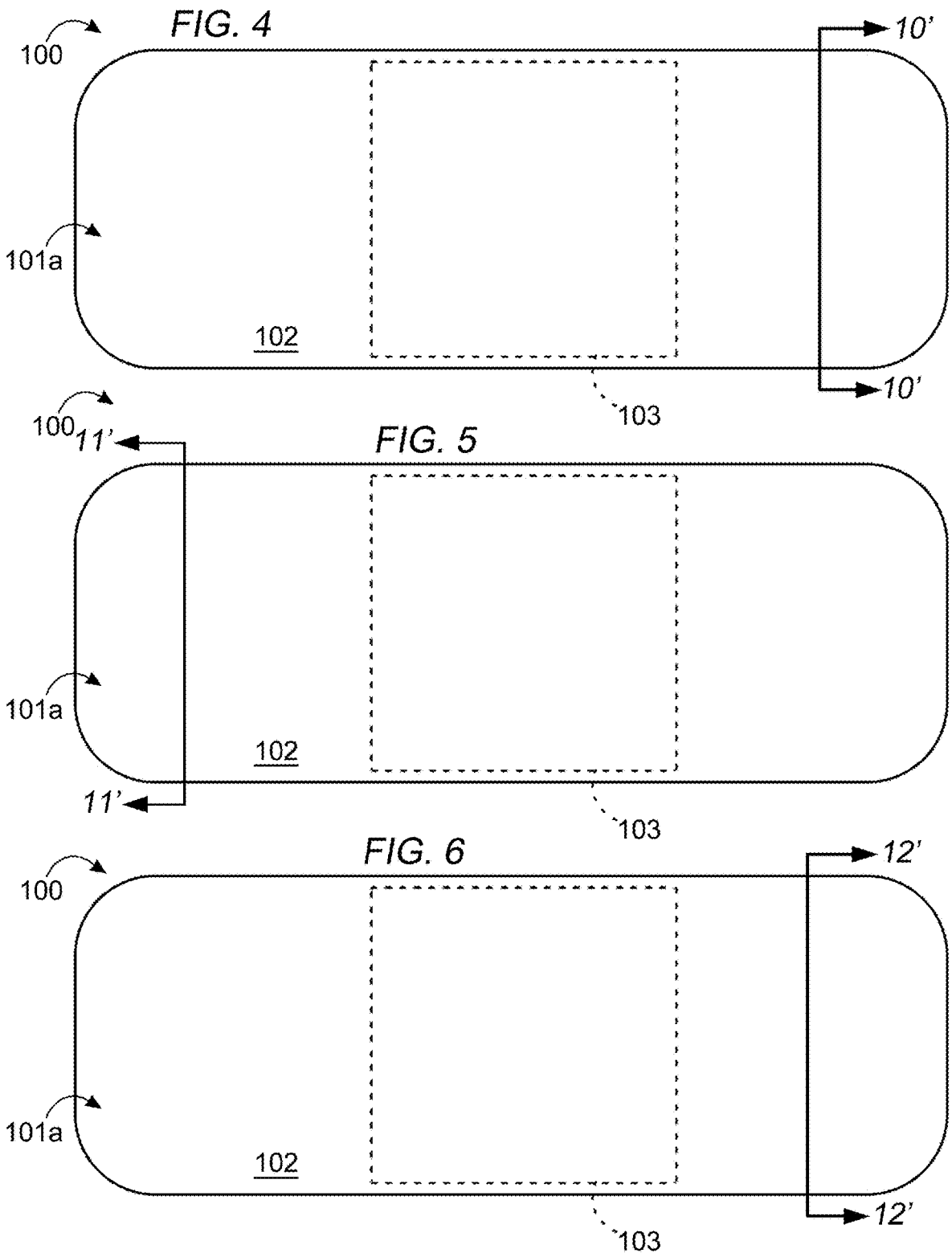

PAINLESS BANDAGE REMOVAL SYSTEM

FIELD OF THE INVENTION

The present invention relates generally to bandages and more particularly a bandage that includes an adhesive and an adhesive solvent release agent.

BACKGROUND OF THE INVENTION

Bandages are long known in the art and are covers of various sizes and shapes that typically include a pad portion that may or may not be absorbent, and are made to be placed over wounds or incisions in order to keep the area clean and to prevent infection. By design, many bandages include an adhesive agent that is made to adhere well to the skin and to resist the effects of moisture, body secretions and sweat. Adhesive strength is advantageous until the bandage must be removed, which often is a painful process for the patient, especially if the adhesive portions are adhered over hair or sensitive skin. Moreover, adhesive remaining on the skin may collect debris and become a breeding ground for bacteria.

With varying success, attempts have been made to design an adhesive bandage which may be removed painlessly. Such "painless" adhesive bandages tend to fall broadly in two categories: those that rely on a solvent which is released by breaking a seal separating the solvent and the adhesive in order to dissolve the adhesive agent, and others which rely on heating the adhesive directly until it degrades sufficiently to remove the bandage from the skin without sticking. In the first case, liquid solvents are difficult to segregate from the adhesive layer and accidental breaking of the seal during bandage application means a wasted bandage. In the second case, application of heat sufficient to directly degrade the adhesive is typically painful for the patient. In addition, various heat deactivated bandages described in the art are either deactivated at a temperature too low to be practical such as 30 Celsius, in which case the bandage may fall off when exposed to normal human body temperature, or, the adhesive deactivation temperature is excessively high, in which case the patient may suffer pain when the heat is applied.

What is needed is an adhesive bandage that includes an adhesive which is indirectly degradable by a heat source that activates an adhesive release agent. It would be desirable if the temperature at which the adhesive release agent is activated is sufficiently high so that undesirable loosening of the bandage does not occur under normal circumstances, and also sufficiently low so that the patient experiences no pain from heat application when the bandage is removed.

SUMMARY OF THE INVENTION

In a broad exemplary implementation according to the present invention, a painless bandage removal system comprises a solvent degradable pressure sensitive adhesive which may be selected from one or more of the following polymer groups: acrylic, rubber, silicone, polyether, polyester, polyurethane and ethylene-vinyl acetate. More specifically, commonly used bandage adhesives that may be used include methacrylates, tetrahydrofurfuryl acrylate, p-tertbutylphenol formaldehyde resin and epoxy diacrylates. Accordingly, various implementations according to the present invention may use any one or combination of the foregoing adhesives, or any other adhesive as would be appreciated by those skilled in the art with access to this disclosure. The bandage removal system also includes an adhesive solvent release agent, and a bandage cover to which one or more layers of the adhesive and one or more layers of the adhesive solvent release agent are adhered.

In an aspect combinable with the foregoing exemplary implementation, the adhesive solvent release agent is heat activated.

In an aspect combinable with any of the previous aspects, the bandage includes microbeads in a layer adjacent to the adhesive.

In an aspect combinable with any of the previous aspects, the microbeads may include in combination or individually, a short chain paraffin-type wax, a mineral oil, a microcrystalline wax, a sterin, a mixture of a short chain paraffin-type wax with mineral oil, or a petroleum jelly.

In an aspect combinable with any of the previous aspects, the microbeads may be homogeneous throughout, or may include an outer shell of a first material having a relatively higher temperature melting point, and a core of a second material with a relatively lower melting point.

In an aspect combinable with any of the previous aspects, the microbeads may be placed in grooves or channels between regions of the adhesive layer (e.g., within a grid work of channels incised or otherwise formed within the adhesive layer).

In an aspect combinable with any of the previous aspects, a generally homogeneous region of microbeads and a generally homogeneous region of adhesive may be configured with one generally homogeneous region extending into the other, e.g., protrusions of the microbead layer into the adhesive layer.

In an aspect combinable with any of the previous aspects, a fibrous material; e.g., a cellulose based non-woven material, may reside between a generally homogeneous region of microbeads and a generally homogeneous region of adhesive.

In an aspect combinable with any of the previous aspects, the bandage may have a skin contacting layer that includes a generally homogeneous layer of adhesive.

In an aspect combinable with any of the previous aspects, a layer of microbeads may reside between the bandage cover and the generally homogeneous layer of adhesive comprising the skin contacting surface of the bandage.

In an aspect combinable with the any of the previous aspects, a non-homogenous adhesive layer may include a suspension of microbeads interspersed in the adhesive layer.

In an aspect combinable with the any of the previous aspects, the bandage may include a gradient of a generally homogeneous adhesive layer that transitions to a generally non-homogenous layer that includes microbeads.

In an aspect combinable with the any of the previous aspects, the bandage system may include an air-activated chemical compound defining an exothermic agent.

In an aspect combinable with any of the previous aspects, the air-activated chemical compound may be contained in a air tight pouch forming a separate layer in the bandage, wherein the compound is activated by peeling, severing or rupturing a sealing membrane of the pouch.

BRIEF DESCRIPTION OF DRAWINGS

FIG. 1 is a top plan view of one implementation according to the present invention;

FIG. 2 is a top plan view of a second implementation according to the present invention;

FIG. 3 is a top plan view of a third implementation according to the present invention;

FIG. 4 is a top plan view of a fourth implementation according to the present invention;

FIG. 5 is a top plan view of a fifth implementation according to the present invention;

FIG. 6 is a top plan view of a sixth implementation according to the present invention;

DETAILED DESCRIPTION OF THE INVENTION

Figure 7:
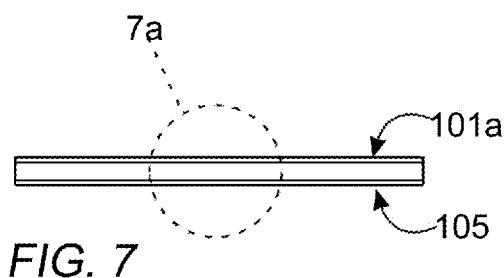
FIG. 7 is a cross-sectional view taken along lines 7'-7' of (FIG. 1) shown with exaggerated thickness for purposes of clarity.

Reference Listing of Elements 100 bandage
101a bandage top,
101b bandage bottom
102 film or fabric cover
103 pad
104 adhesive agent
105 skin contacting surface
106 homogeneous composition
107 non-homogenous composition
108 microbeads
109 fibrous material
110 solvent release agent
112 peel away backing
113 filamentous layer
114 channel
115 exothermic agent
116 separating membrane
117 pouch
118 filament or tab
119 seal
200 heat source Definitions In the following description, the term "bandage" refers to a cover, typically with some padding that is placed over wounds, incisions or other possible entry points for infection. The term "exothermic" refers to chemical reactions where heat energy is released. The words "film" and "membrane" may be used interchangeably. The term "solvent" means a compound that is capable of breaking the adhesive bonds of adhesives of a type used in adhesive bandages. When describing an adhesive herein, "homogeneous composition" refers to an adhesive layer that does not include an adhesive solvent release agent intermixed therewith. The term "non-homogenous" refers to an adhesive layer that may include a dispersion of microbeads within the adhesive layer, or an adhesive layer surrounding one or more layers of microbeads. Regarding microbeads, the term "homogeneous composition" means that the shell and the core of the microbead are the same material, while the term "non-homogenous" means the shell and the core are different materials. The singular terms "a", "an", and "the" include plural referents unless the context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. It should be understood that the objects, features and aspects of any embodiment disclosed herein may be combined with any object, feature or aspect of any other embodiment without departing from the scope of the invention. The term "comprises" means "includes." All publications, patent applications, patents, and other references mentioned herein are incorporated by reference in their entirety for all purposes. In case of conflict, the present specification, including explanations of terms, will control. In addition, the materials, methods, and examples are illustrative only and not intended to be limiting.

Referring generally to FIGS. 1-14B, a painless bandage removal system includes a bandage with a cover 102 that may be a fabric, a non-woven material, a fibrous cellulose, a plastic film composition or any material which would suggest itself to one skilled in the art. The cover may include a pad portion 103 of any thickness depending on the bandage application. On a side 105 of the bandage configured to attach to skin is an adhesive layer of an adhesive agent 104 that may be a homogeneous composition 106 or non-homogenous composition 107. In certain implementations according to the present invention, the non-homogenous adhesive layer includes a suspension of heat activatable microbeads 108. The microbeads 108 include an adhesive solvent release agent 110 capable of degrading the adhesive agent 104 when the microbeads are liquefied by the application of heat and then intermingle with the adhesive layer. A peel away strip 112 that would typically be removed to expose the skin contacting surface 105 of the bandage prior to its application to skin has been omitted from the drawing figures for purposes of clarity.

Microbeads

Microencapsulation typically refers to small bodies between 1μ and 1 mm dia. One method of producing the microbeads also known as microcapsules, for use in various implementations described by this disclosure is by "prilling" or spray-drying which are methods of producing small diameter generally spherical bodies of various composition.

Heated droplets, usually sprayed, are exposed to a temperature gradient such as in a prilling tower and solidify upon entering cooler regions of the tower. Depending on the chemical composition of the droplets, the resulting microbeads may be homogenous or non-homogenous. In some cases, the microbeads may include an outer surface or shell, that encapsulates contents of a different composition. Encapsulated contents may have a higher or lower melting point than the surrounding shell. In some cases, a shell composed of a first waxy composition may have a higher melting point than an encapsulated waxy composition. For example, a shell material may liquefy at 45° C. while an encapsulated material may liquefy at 43° C. In some cases, a soft shell may be comprised of a gelatin and a plasticizer such as glycerine or sorbitol. The soft shell may contain a core of hydrophobic material such as a mineral oil. Aqueous phase coacervation, may be used to encapsulate a paraffin-type core with outer shell of a gelatin. Mayya et al., describes in "Micro-encapsulation by complex coacervation: influence of surfactant" *Polymer Intl.* vol. 52, 2003, pp. 644-647, a method of encapsulating a paraffin oil within a gelatin and arabic gum complex. While in food science it is often desirable for gelatin based shells with encapsulated contents intended for enteric release to typically possess a Bloom strength between 220 and 500, however, for implementations according to the present invention a much lower Bloom strength (e.g., 50-150) is desirable as well as a lower melt temperature. Gelatin derived from the skin, bones and connective tissues of cattle and pigs typically has a moderate to high Bloom strength. Gelatin derived form marine sources, e.g., fish gelatin is available with lower melting points and lower bloom values than gelatin derived from terrestrial sources. Piacentini et al., describes in "Microencapsulation of oil droplets using cold water gelatine/gum arabic complex coacervation by membrane emulsification" *Food Research Intl.* vol. 53, no. 1, 2013, pp. 362-372, a method of encapsulating food grade sunflower oil within a glutaraldehyde crosslinked shell of fish gelatin and gum arabic.

FIGS. 1-5 depict top plan views of adhesive bandages that share a common shape. It should be understood that the pattern and dimensions depicted are merely exemplary. Persons having skill in the art and access to this disclosure will appreciate other suitable patterns and dimensions, e.g., circular, square or strip. The particular rectangular shape depicted that includes a central pad 102 with adjacent adhesive flaps is provided because of its familiarity and to aid in understanding the implementations described herein. Some implementations of the present invention may or may not include a pad portion 103, while in other implementations a pad portion may encircled by adhesive regions. The bandage may include a single adhesive region, multiple adhesive regions, and the adhesive regions may be contiguous or non-contiguous, being separated by non-adhesive elements such as padding.

Figure 7A:
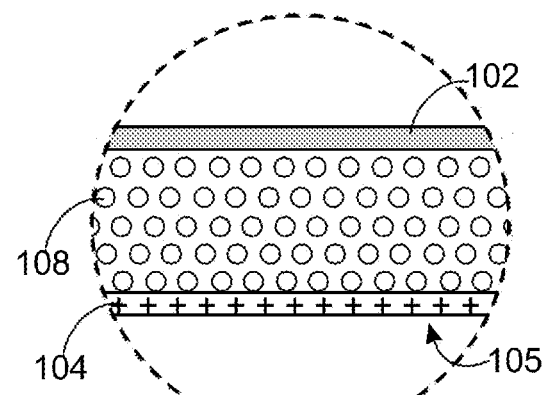
FIG. 7a is a detail view of call-out 7a of (FIG. 7)

FIG. 7A is an enlarged view of callout 7a of FIG. 7, and shows a top side of the bandage cover 102, beneath which is a microbead 108 layer followed by a generally homogeneous layer of adhesive 106. The microbeads are comprised of a wax, an oil, a fatty acid, a sterin or a petroleum based gel that is solid or semi-solid at room temperature, and that is configured to liquefy when the cover 102 is exposed to sufficient heat, e.g., via a hair dryer set to low heat, or a heat lamp beam directed to the cover. In some implementations, the liquefying heat range is preferably between 42° C. and 46° C., more preferably between 43° C. and 46° C., and still more preferably between 44° C. and 46° C.

Figure 8:
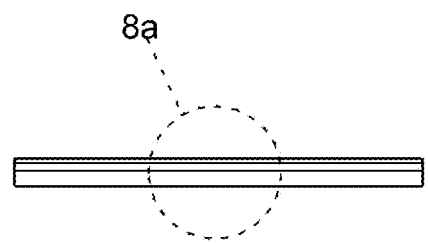
FIG. 8 is a cross-sectional view taken along lines 8'-8' of (FIG. 2) shown with exaggerated thickness for purposes of clarity.
Figure 8A:
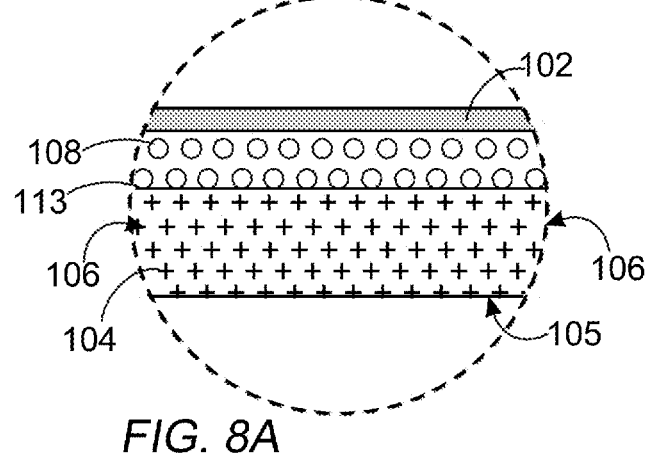
FIG. 8A is a detail view of call-out 8a of (FIG. 8)

FIG. 8A is an enlarged view of callout 7a of FIG. 8, and shows a relatively thicker layer of adhesive 106 adjacent a relatively thinner layer of microbeads. The microbeads may be abutting one another, or the microbeads may be suspended in a matrix that includes a fibrous material 109 (e.g., a cellulose composition). When heat is applied to the cover 102, constituents of the microbeads liquify and are dispersed within the adhesive layer in order to degrade the adhesive bonds. The adhesive layer may be a relatively homogeneous composition that includes an acrylate or other category of adhesive, or the adhesive layer may be non-homogenous and include a fibrous material 109 that provides a capillary conduit for oils released by the liquefied microbeads thus effecting even dispersion of the microbead contents.

Figure 9:
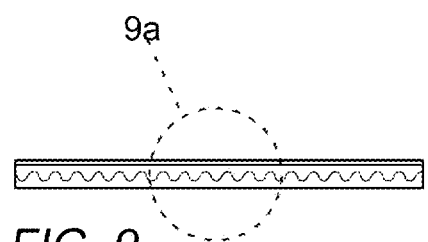
FIG. 9 is a cross-sectional view taken along lines 9'-9' of (FIG. 3) shown with exaggerated thickness for purposes of clarity.
Figure 9A:
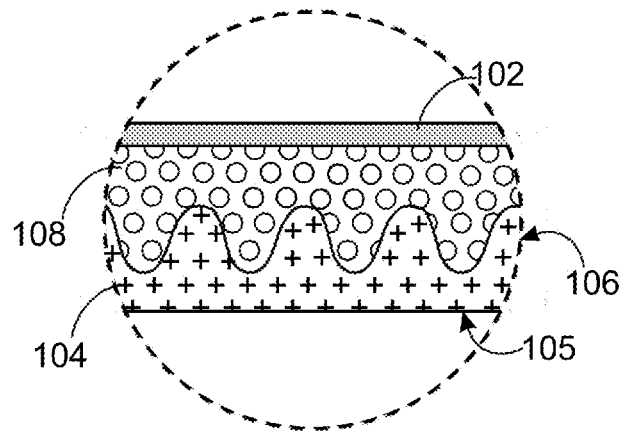
FIG. 9A is a detail view of call-out 9a of (FIG. 9)

FIG. 9A is an enlarged view of callout 9a of FIG. 9, and shows a layer of microbeads that includes ridges that extend into troughs of the adhesive layer 106 in order that the liquefied microbead contents penetrate the adhesive layer quickly.

Figure 10:
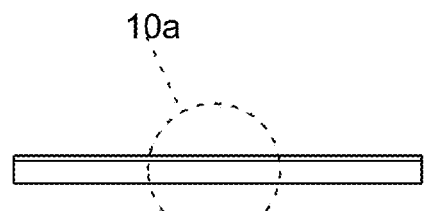
FIG. 10 is a cross-sectional view taken along lines 10'-10' of (FIG. 4) shown with exaggerated thickness for purposes of clarity.
Figure 10A:
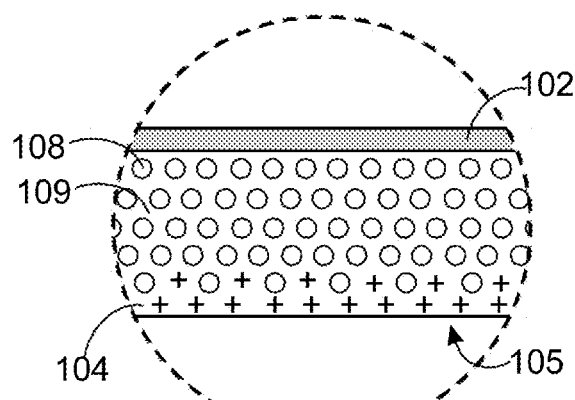
FIG. 10A is a detail view of call-out 10a of (FIG. 10)

FIG. 10A is an enlarged view of callout 10a of FIG. 10, and shows an implementation where the skin contacting surface of the bandage is faced with adhesive agent 104 in a gradient with microbeads 108. Both the microbeads and the adhesive agent may be in a matrix of a fibrous material.

Figure 11:
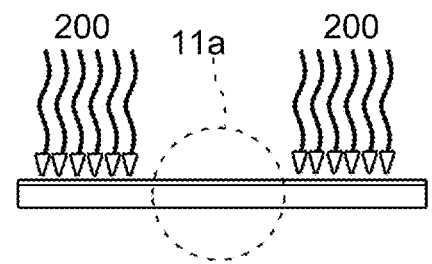
FIG. 11 is a cross-sectional view taken along lines 11'-11' of (FIG. 5) shown with exaggerated thickness for purposes of clarity.
Figure 11A:
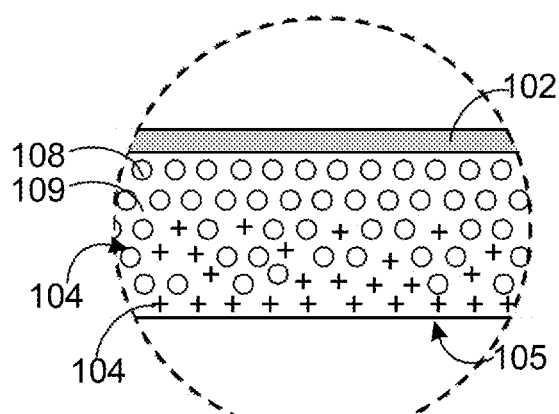
FIG. 11A is a detail view of call-out 11a of (FIG. 11)

FIG. 11A is an enlarged view of callout 11a of FIG. 11, and shows an implementation where the adhesive/microbead gradient is less defined, and the gradient constituents more evenly suspended than in the foregoing implementations.

Figure 12:
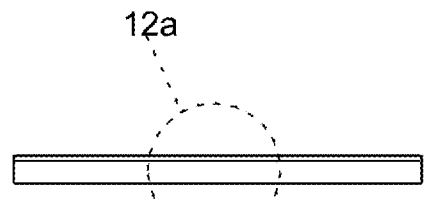
FIG. 12 is a cross-sectional view taken along lines 12'-12' of (FIG. 6) shown with exaggerated thickness for purposes of clarity.
Figure 12A:
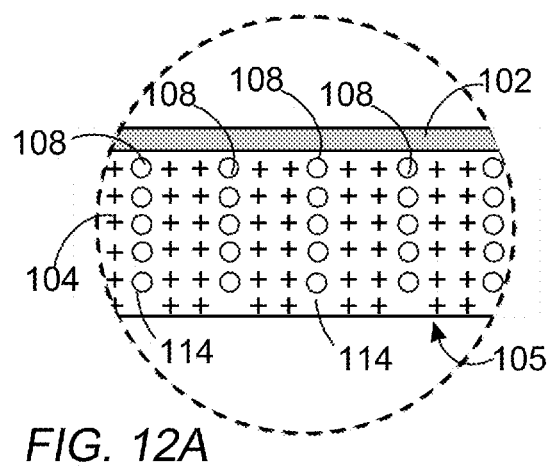
FIG. 12A is a detail view of call-out 12a of (FIG. 12)
Figure 13:
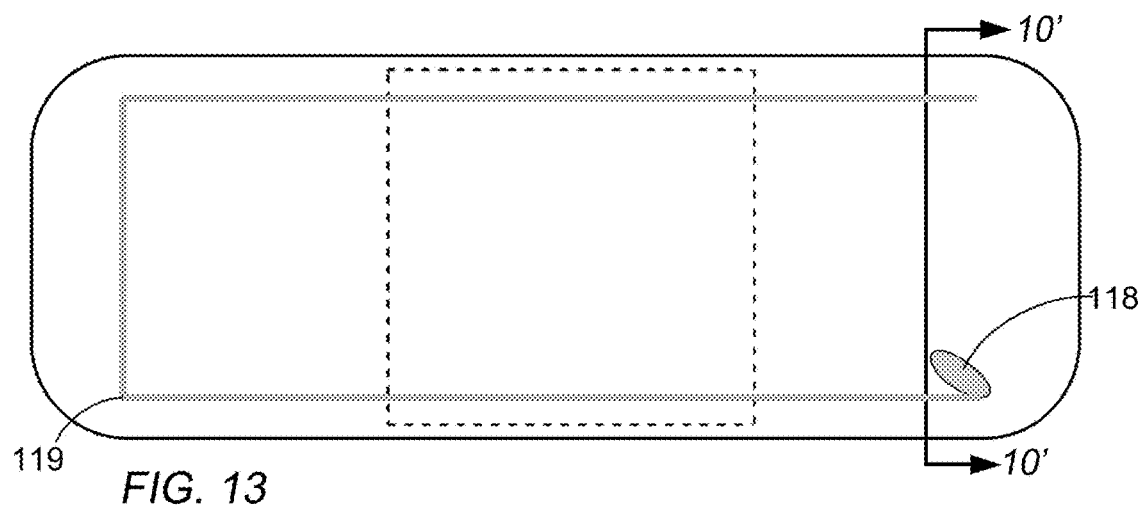
FIG. 13 is a top plan view of another implementation according to the present invention.

FIG. 12A is an enlarged view of callout 12a of FIG. 12, and shows an implementation that includes regions of adhesive agent that are separated by channels containing microbeads 108. While in the particular implementation shown, the microbeads do not extend to the skin contacting surface of the bandage, the microbead containing channels can be any depth and may extend to the skin contacting surface 105. In cases where the microbeads do not extend to the skin contacting surface, a thin layer of adhesive agent 104 may cover the microbead containing channels.

Figure 14:
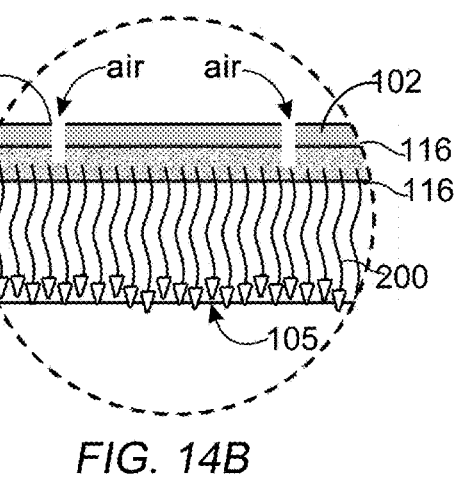
FIG. 14 is a cross-sectional view taken along lines 14'-14' of (FIG. 13) shown with exaggerated thickness for purposes of clarity.
Figure 14A:
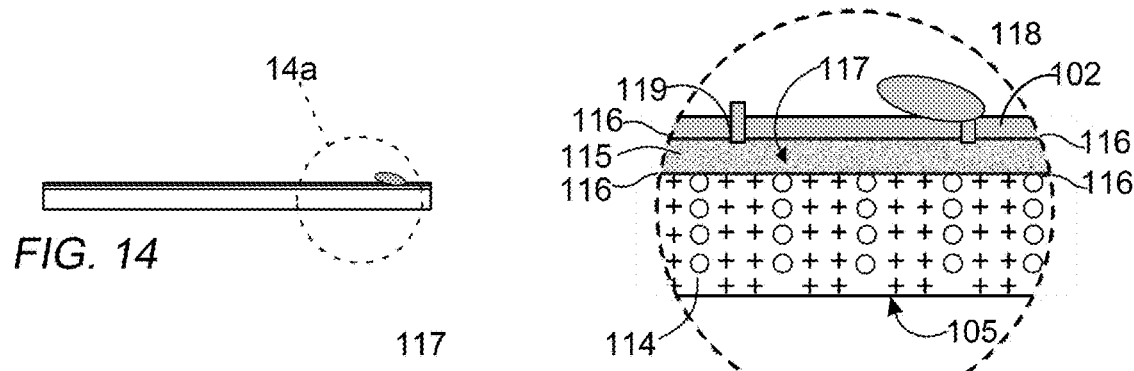
FIGS. 14A and 14B are detail views of call-out 14a of (FIG. 13), showing respectively, the pre-activation state and activated state of exothermic agent 115.
Figure 14B:
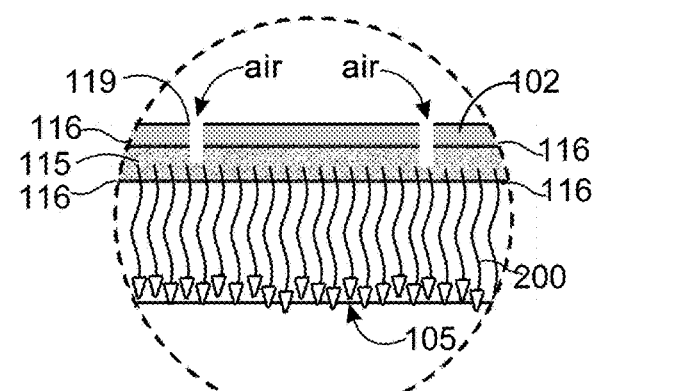

FIG. 14A is an enlarged view of callout 14a of FIG. 14, and shows an implementation that includes a portion of an exothermic agent 115 that may be a chemical compound or mixture contained in an air tight pouch, the contents of which when exposed to air, produce an exothermic reaction. Such chemical compounds and mixtures are known in the art and typically employed in hand warmers and the like. Generally, the chemical compound or mixture includes iron particles or iron powder and salt water suspended in a matrix of an absorbent such as activated charcoal, polyacrylate or vermiculite. When exposed to air, the iron is oxidized to $Fe_2O_3$ and heat is released. Those with skill in the art and access to this disclosure will recognize that the amount of iron can be increased or reduced to produce a desired temperature range and a desired reaction time. The bandage includes a cover and an air tight pouch 117 with contents residing beneath the cover 102. The pouch contents are exposable to the air by tearing a tab 118 located on the cover 102. The tab may be connected to a filament or string that itself forms a seal 119 of the air tight pouch. In FIG. 14B for example, when tab 118 is pulled, the string is pulled free of the seal and the pouch contents are exposed to air. Because extended reaction times and high heat are not desirable for the particular use to which the present invention is directed, the exothermic agent 115 within the absorbent matrix and all necessary constituents can exist in a thin layer (e.g., 1.5-2 mm) within the air tight pouch. Consistent with previously described implementations, the particular arrangement of the microbead and adhesive layer may vary accordingly. For example, a relatively homogeneous layer of microbeads may reside between the pouch 117 and the adhesive layer. Microbeads may be suspended within an adhesive layer between the pouch and the skin contacting surface of the bandage. The adhesive agent may be suspended within a microbead layer between the pouch and the skin contacting surface of the bandage. Microbeads and adhesive may exist in a gradient between the pouch and the skin contacting surface of the bandage.

In a typical use, the adhered bandage is loosened painlessly by the application of heat 200 which may be obtained by using a hair dryer on a low heat setting. If supplied with a layer of a chemical compound that produces an exothermic reaction when exposed to the air, the heat 200 produced will be sufficient to loosen the bandage adhesive without causing discomfort.

It should be understood that the drawings and detailed description herein are to be regarded in an illustrative rather than a restrictive manner, and are not intended to be limiting to the particular implementations, forms and examples disclosed. For example, adhesive patches carrying transdermal or topical analgesic medicines, bandages and tapes for veterinarian use, kinesiologic tape and any other tapes for non-medical use that are adhered to the skin may make use of the many features, object and aspects of the disclosed implementations Accordingly, it is intended that this disclosure encompass any further modifications, changes, rearrangements, substitutions, alternatives, design choices, and embodiments as would be appreciated by those of ordinary skill in the art having benefit of this disclosure, and falling within the spirit and scope of the following claims.

What is claimed is:

1. A bandage system comprising:
   a cover with a top side and a bottom side;
   an adhesive agent;
   a solvent;
   a thin layer of air activatable chemical compound capable of an exothermic reaction, the thin layer includes an oxidizable component and is disposed with an air tight pouch, the pouch is disposed beneath the cover;
   a heat activated adhesive solvent release agent including a plurality of microbeads, and wherein the adhesive agent and the release agent are adhered to a bottom side of the pouch;
   a displaceable member on the cover defining a seal of the air tight pouch configured to displaceably unseal and expose the thin layer of air activatable chemical compound to air.

2. The bandage system according to claim 1 further comprising a breachable air resistant membrane, and wherein the thin layer of air activatable chemical compound is no more than 2 millimeters in thickness.

3. The bandage system according to claim 1 comprising a layer of the plurality of microbeads, a layer of the heat activated adhesive agent and the thin layer of the air activatable chemical compound.

4. The bandage system according to claim 1 comprising a skin contacting layer configured for direct skin contact and the adhesive agent is substantially homogeneous.

5. The bandage system according to claim 1, the adhesive agent including a gradient of a generally homogeneous composition configured to transition to a generally non-homogenous composition, the generally non-homogenous composition including the plurality of microbeads.

6. The bandage system according to claim 1 comprising a matrix of the plurality of microbeads and the adhesive agent.

7. The bandage system according to claim 1 wherein the solvent is taken from one or more of the following: paraffin wax, mineral oil, microcrystalline wax, fatty acid, sterin.

* * * * *